(12) United States Patent
Sundaram et al.

(10) Patent No.: US 10,494,493 B1
(45) Date of Patent: Dec. 3, 2019

(54) NITRIC OXIDE-RELEASING PACKAGING MEMBRANES

(71) Applicant: University of Georgia Research Foundation, Inc., Athens, GA (US)

(72) Inventors: Jaya Sundaram, Watkinsville, GA (US); Jitendra Pant, Athens, GA (US); Marcus J Goudie, Athens, GA (US); Sudhagar Mani, Watkinsville, GA (US); Hitesh Handa, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 237 days.

(21) Appl. No.: 15/595,897

(22) Filed: May 15, 2017

Related U.S. Application Data

(60) Provisional application No. 62/336,469, filed on May 13, 2016.

(51) Int. Cl.

| | | |
|---|---|---|
| *B32B 23/14* | (2006.01) | |
| *C07C 207/00* | (2006.01) | |
| *C08K 5/43* | (2006.01) | |
| *C08L 1/00* | (2006.01) | |
| *C08L 5/08* | (2006.01) | |
| *C08J 5/22* | (2006.01) | |
| *C08G 12/22* | (2006.01) | |
| *B32B 27/34* | (2006.01) | |
| *C08L 3/00* | (2006.01) | |
| *H01J 37/28* | (2006.01) | |

(52) U.S. Cl.
CPC .............. *C08J 5/2256* (2013.01); *B32B 23/14* (2013.01); *B32B 27/34* (2013.01); *C07C 207/00* (2013.01); *C08G 12/22* (2013.01); *C08K 5/43* (2013.01); *C08L 3/00* (2013.01); *C08L 5/08* (2013.01); *B32B 2307/7163* (2013.01); *B32B 2317/18* (2013.01); *B32B 2439/70* (2013.01); *H01J 37/28* (2013.01)

(58) Field of Classification Search
CPC ...................................................... B65D 81/28
See application file for complete search history.

(56) References Cited

U.S. PATENT DOCUMENTS

| | | | |
|---|---|---|---|
| 2006/0246242 A1* | 11/2006 | Siegel | A23B 4/10 428/34.1 |
| 2012/0216718 A1* | 8/2012 | Berglund | D21H 11/18 106/487 |

* cited by examiner

*Primary Examiner* — Ramsey Zacharia
(74) *Attorney, Agent, or Firm* — Thomas|Horstemeyer, LLP

(57) ABSTRACT

Biodegradable composite membranes with antimicrobial properties consisting of nanocellulose fibrils, chitosan, and S-Nitroso-N-acetylpenicillamine (SNAP) were developed and tested for food packaging applications. Nitric oxide donor, SNAP was encapsulated into completely dispersed chitosan in 100 mL, 0.1N acetic acid and was thoroughly mixed with nanocellulose fibrils (CNF) to produce a composite membrane. The fabricated membranes had a uniform dispersion of chitosan and SNAP within the nanocellulose fibrils, which was confirmed through Scanning Electron Microscopy (SEM) micrographs and chemiluminescence nitric oxide analyzer. The membranes prepared without SNAP showed lower water vapor permeability than that of the membranes with SNAP. The addition of SNAP resulted in a decrease in the Young's modulus for both 2-layer and 3-layer membrane configurations. Antimicrobial property evaluation of SNAP incorporated membranes showed an effective zone of inhibition against bacterial strains of *Enterococcus faecalis*, *Staphylococcus aureus*, and *Listeria monocytogenes* and demonstrated its potential applications for food packaging.

16 Claims, 7 Drawing Sheets

TABLE 1

| Membrane type | Water vapor permeability (kg.m/ m².day.Pa) | Membrane thickness (mm) |
|---|---|---|
| Chitosan | $7.01 \times 10^{-6}$ | 0.058 |
| Nano Cellulose Fibrils (CNF) | $6.88 \times 10^{-6}$ | 0.060 |
| 2-layer CNF + Chitosan with SNAP | $1.56 \times 10^{-5}$ | 0.126 |
| 2-layer CNF + Chitosan without SNAP | $8.81 \times 10^{-6}$ | 0.068 |
| 3-layer CNF + Chitosan with SNAP | $1.11 \times 10^{-5}$ | 0.124 |
| 3-layer CNF + Chitosan without SNAP | $8.31 \times 10^{-6}$ | 0.096 |

FIG. 6

| Film type | Bacterial strain | ZOI (mm) |
| --- | --- | --- |
| 2-layer SNAP incorporated chitosan-CNF films | *S. aureus* | 30 |
| 3-layer SNAP incorporated chitosan-CNF films | *S. aureus* | 30 |
| 2-layer SNAP incorporated chitosan-CNF films | *E. faecalis* | 34 |
| 3-layer SNAP incorporated chitosan-CNF films | *E. faecalis* | 35 |
| 2-layer SNAP incorporated chitosan-CNF films | *L. monocytogenes* | 37 |
| 3-layer SNAP incorporated chitosan-CNF films | *L. monocytogenes* | 45 |

FIG. 7

NITRIC OXIDE-RELEASING PACKAGING MEMBRANES

BACKGROUND

The Centers for Disease Control and Prevention (CDC), estimates that one in every six Americans gets sick from foodborne illness each year, results in 128,000 hospitalizations and 3,000 deaths. Foodborne pathogens deteriorate the quality of food, causing increased food wastage. Recent foodborne microbial outbreaks are driving a search for innovative ways to inhibit microbial growth in foods while maintaining quality, freshness, and safety and extend the shelf-life of fresh produces. The Federal government advises and encourages healthy eating habits, which includes consumption of a variety of fresh fruits and vegetables[1,2]. As a result, the per capita consumption of eating fresh produce has increased to $12 billion annual sales in the past few years[3,4] and the fresh-cut food industry sector becomes the fastest growing segment of food industries. As the fresh-cut produce market continues to grow, such producers face the challenge of an increase in microbial safety for longer shelf life. From 1996 to 2006, 22 foodborne illness outbreaks were associated with the consumption of fresh produce. Of these outbreaks, according to Food and Drug Administration (FDA), 18 outbreaks were implicated by fresh-cut produce. Foodborne illness outbreaks also impact the fresh produce trade leading to economic losses[4]. Food related epidemic can be prevented by means of improved surveillance and detection of contaminations, enhanced epidemiological investigation, safe packaging, and effective methods to identify pathogens[5-10].

The packaging of fresh fruits and vegetables is one of the most important steps in the long supply chain from the producer to the consumer. Protecting the fresh produce by packing them in antimicrobial (AM) films can extend their shelf life of food[11-14]. They also effectively control the foodborne pathogens and food-spoiling microorganisms. These packages are typically manufactured by incorporating antimicrobial agents, immobilized or coated on the surface of the packaging material. Even though the AM packaging films and number of antimicrobial agents have been studied for many years, commercial successes of these packaging materials are very limited due to many constraints in large scale production[15]. Selection of packaging systems and the antimicrobial agents are very critical as they would influence the inherent physicochemical properties of food. Now there is also an increasing demand for green labeling and environmental safety, leading to an increasing number of R & D efforts in the field of biodegradable food packaging materials. Instead of using polymer materials derived from petroleum products, biopolymers derived from renewable sources (starch, cellulose, protein etc.) are more favorable in developing an eco-friendly packaging system for food. When the antimicrobial agents are combined with biodegradable packaging materials, it features the merits of the packaging system in terms of food safety, shelf-life, and environmental friendliness.

Cellulose is one of the most abundantly available biopolymers and it is a linear carbohydrate polymer chain that contains D-glucopyranose units joined together by β-1,4-glycosidic linkages. The cellulose pulp derived from plants and trees are either mechanically or chemically fibrillated into nanocellulose fibrils (CNF) having 5-20 nm diameter. These nanocellulose fibrils highly influence the properties and functionality of the final products[16-19]. George et al made food packaging membranes using nanocellulose derived from bacterial cellulose and demonstrated its relevance as a packaging material for the food industry[20]. The prepared membrane possessed minimal oxygen permeability, good mechanical stability, and controlled water permeability, which are critical for food packaging materials to maintain the quality of packed food. Reinforcing nanocellulose with other long chain polymers such as chitosan to develop biodegradable nanocomposite food packaging materials can further improve the quality of the packaging material as well as long storage life[21].

Antimicrobial films with controlled release of antimicrobial agents are more advantageous than dipping or spraying the food with antimicrobial agents containing edible polymers[22-24]. In these types of coatings, the antimicrobial activity is lost due to its inactivation by the food components leading to concentrations dropping below active levels[25]. There are several antimicrobial agents available to incorporate into packaging films. However, each one has its own disadvantages apart from their noted advantages. Sodium nitrite salt has been used for centuries in meat curing. Nitric oxide (NO) released from this salt terminates free radicals present in lipid oxidation and provide the typical property for the cured meat[26]. There are many NO-donating compounds such as nitrates and nitrites that have been used for several years in curing and preserving meats, fish, and certain cheeses[27, 28]. Nitric oxide inhibits the growth of wide varieties of bacteria (both gram positive and gram negative), viruses, fungi, and yeast[29-31]. The biggest advantage of NO as an antimicrobial agent is its antimicrobial activity against antibiotic-resistant strains[32-34]. However, incorporating NO donor compounds such as S-nitrosothiols in the packaging materials for food has not been yet studied. In this study, we investigated the effects of incorporating the NO donor, S-Nitroso-N-acetylpenicillamine (SNAP) into biodegradable nanocellulose-chitosan composite membranes for increased antimicrobial activity for potential food packaging application.

BRIEF SUMMARY

An embodiment of the present disclosure includes a packaging film or membrane comprising an antibacterially effective amount of a monomer or polymer comprising an S-nitrosothiol functional group.

Another embodiment of the present disclosure includes a multilayer packaging film comprising at least one layer comprising an antibacterially effective amount of a monomer or polymer comprising an S-nitrosothiol functional group.

Another embodiment of the present disclosure comprises a packaging film comprising an antibacterially effective amount of a monomer or polymer comprising an S-nitrosothiol functional group and a biodegradable polymeric structure.

Another aspect of the present disclosure comprises a method of preparing a packaging film comprising combining a packaging film comprising an antibacterially effective amount of a monomer or polymer comprising an S-nitrosothiol functional group and at least one other packaging film layer.

Another aspect of the present disclosure comprises a method for preserving a foodstuff comprising enclosing the foodstuff in a packaging film a packaging film comprising an antibacterially effective amount of a monomer or polymer comprising an S-nitrosothiol functional group.

BRIEF DESCRIPTION OF THE FIGURES

FIG. 6 is Table 1 which shows the water permeability of different types of packaging membranes.

FIG. 7. Is Table 2 which is a comparative analysis of zone of inhibition among different bacterial strains using developed antimicrobial packaging membranes.

DETAILED DESCRIPTION OF EMBODIMENTS OF THE INVENTION

Figure 1:
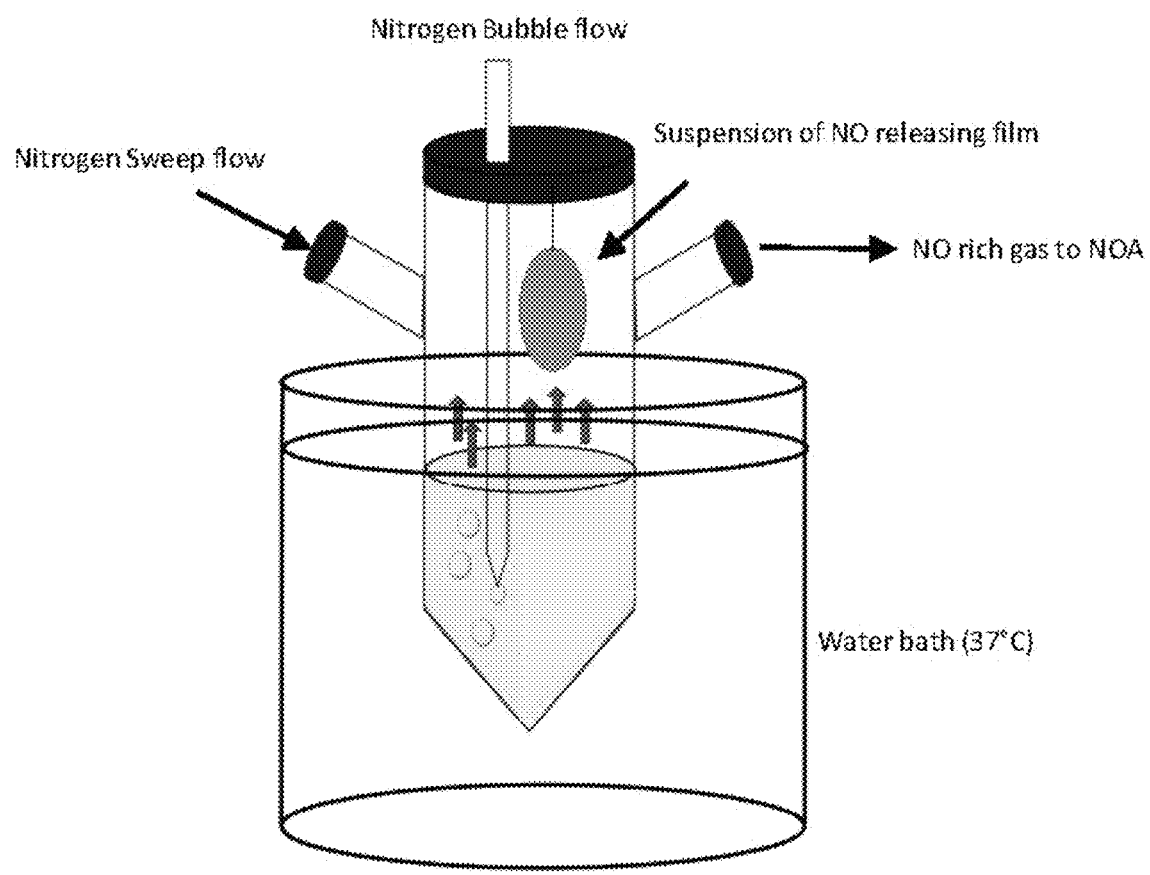
FIG. 1 is representation of test configuration for an NOA cell for measurement of NO released from chitosan films in a humid environment.

The present invention, as well as features and aspects thereof, is directed towards providing a packaging film or membrane comprising an antibacterially effective amount of a monomer or polymer comprising an S-nitrosothiol group. By the term "antibacterially effective amount" is meant the amount of monomer and/or polymer comprising the S-nitrosothiol group effective to kill bacterial or fungus on or proximate to a foodstuff enclosed by the packaging film for the duration of an intended storage time of the enclosed foodstuff.

In an embodiment, the storage time may be from 1 day to 30 days, or from 1 day to 20 days, or from 1 to 10 days, or from 1 to 5 days, or from 1 to 3 days.

In an embodiment, the polymer or monomer may be a monomer, for example an organic molecule comprising an S-nitrosothiol functional group. The monomer may be incorporated as a monomer within a polymeric matrix, or may be covalently bound to a polymeric matrix, e.g., co-polymerized with one or more mers, e.g., monomers. In an embodiment, the monomer may comprise an amino acid moiety, e.g., an amino acid comprising a thiol group. For example, the monomer may be S-Nitrosoglutathione, S-nitrosocysteine, or S-Nitroso-N-acetylpenicillamine; or a salt, chelate, or derivative thereof.

By a salt or derivative thereof is meant, e.g., a salt of the carboxyl group (COOH) of the monomer, or e.g., an ester or amide of the carboxyl group (COOH) of a monomer, or e.g., an amine salt of an amino moiety of a monomer (e.g., RNH2); or another salt, chelate, or derivative thereof as understood by those of skill in the art.

In an embodiment, the percentage of monomer in the packaging layer is from about 0.1% to about 20%, or from about 0.1% to about 10%, or from about 0.1% to about 5%, or from about 0.1% to about 1%, or from about 0.5% to about 1% by weight.

The biodegradable polymer may include polymers prepared from one or more monomers or polymers. The biodegradable polymer may comprise a hydrophilic and/or a hydrophobic polymer. Such starting materials include a chitosan, nano-clay, alumina, a microcellulose, a nanocellulose, or a fibril thereof, e.g., a nanocellulose fibril.

The amount of the biodegradable polymer in the packaging layer may be from 90% to 99.9%, or from 95 to 99.9% by weight. In an embodiment, the packaging film may comprise a weight ratio of chitosan to a nanocellulose fiber, e.g., from 10:1 to 1:10, or from 5:1 to 1:5, or from 2:1 to 1:2, or about 1:1. In an embodiment the biodegradable polymer comprising the S-nitrosothiol may be blended with another polymer, e.g., to improve the physical characteristics of the packaging film. For example, the packaging film may be laminated on, or overlayed onto, a polyethylene terephthalate film, or a biaxially oriented polyethylene terephthalate film, a polyvinyl chloride film, a polyvinyl alcohol film, polyethylene glycol film, poly-lactic acid film, and the like.

In an embodiment, the packaging film may provide water transport through the film sufficient to maximize the storage of the enclosed foodstuff. The water transport through the film may be from about 1 g/m$^2$·day to about 50 g/m$^2$·day; or from about 5 g/m$^2$·day to about 30 g/m$^2$·day; or from about 7.0 to about 29 g/m$^2$·day as measured under an accelerated condition of 40° C. temperature and 90% relative humidity. The packaging film may provide oxygen transport through the film varies from 2700 to 0.3 cm$^3$/m$^2$·day·atm at 20° C. temperature and 65% relative humidity.

In an embodiment, the biodegradable polymer comprising an S-nitrosothiol group is a stretchable film, e.g., the packaging film has a tensile strength or Young's modulus acceptable for food packaging may be from 0.1 to 4.0 GPa at 23° C. temperature and 50% relative humidity. In an embodiment the packaging film may provide an NO release sufficient to kill microorganisms and to prevent any spore formation on the surface of the packaging film or in or on the foodstuff enclosed by the packaging film. The NO release rate may be from about $10^{-11}$ to $10^{-9}$ mol/cm$^2$-min, or from $10^{-10}$ to $10^{-9}$ mol/cm$^2$-min.

In an embodiment, the microorganisms controlled by the packaging film include *Listeria* spp., e.g., *Listeria monocytogenes*, *Enterobacteriaceae* spp, e.g. *Salmonella* spp, e.g., *Salmonella enterica*, *Escheria* spp., e.g., Shiga toxin-producing *E. coli* (STEC), e.g., *E. coli* O157:H7, *Vibrio* spp., e.g., *Vibrio vulnificus*, and *Clostridium* spp., e.g., *Clostridium botulinum*, *Staphylococcus* spp., e.g., *Staphylococcus aureus*, *Campylobacter* spp., e.g., *Campylobacter jejuni*.

Materials and Methods

Chitosan (85% deacetylated), glacial acetic acid, glycerol, N-acetylpenicillamine, sulfuric acid, hydrochloric acid, sodium nitrite, potassium chloride, sodium chloride, potassium phosphate monobasic and sodium phosphate dibasic were purchased from Sigma-Aldrich (St. Louis, Mo., USA). Nanocellulose fibrils were bought from the University of Maine, MI. Luria broth (LB)-Lennox and Luria Agar (LA)-Miller were obtained from Fisher Bioreagents (Fair Lawn, N.J.).

Synthesis of S-Nitroso-N-acetyl-D-penicillamine (SNAP)

S-Nitroso-acetyl penicillamine was synthesized using a modified version of a previously reported method by Clough and Thrush (1967). Equimolar ratios of N-acetylpenicillamine (NAP) and sodium nitrite were added to a reaction vessel, which had 1:1 mixture of water and methanol containing 2 M HCl and 2 M H$_2$SO$_4$, and stirred for 30 minutes. The reaction vessel was cooled in an ice bath to precipitate the SNAP crystals. After precipitation of SNAP crystals, they were collected by filtration and washed with water to remove unreacted salts, and air dried. The entire process of SNAP synthesis was protected from light. The purity level of synthesized SNAP was tested using the Sievers Chemiluminescence Nitric Oxide Analyzer and recorded greater than 95%.

Fabrication of composite membrane: Biodegradable antimicrobial packaging membranes were prepared in 2-layer and 3-layer configurations. The 2-layer membranes contained one layer with 2 wt % SNAP in nanocellulose-chitosan with a top coat of nanocellulose-chitosan without SNAP. Similarly, the 3-layer membranes contained the middle layer with 2 wt % SNAP in nanocellulose-chitosan with a top and bottom layers of nanocellulose-chitosan without SNAP. The control 2-layer and 3-layer membranes were prepared separately with nanocellulose-chitosan without SNAP. About 2 wt % of chitosan was completely dispersed in 100 mL of 0.1N acetic acid. In another beaker 2 wt % of nanocellulose fibrils (CNF) was thoroughly dispersed in 100 mL of distilled (DI) water. Completely dispersed CNF and chitosan were then homogeneously mixed together; 3 mL of 80% glycerol was added as a plasticizing agent while mixing them. The resulting mixture was degassed and poured into a clean glass petri dish of 14 cm diameter and air dried. While the drying was incomplete, another set of membrane solution was made as mentioned above and poured on the partly dried membrane as a second layer after 24 hours. On average it took 48 hours to dry for 2-layer control membrane. Similarly, 3-layer control membrane was also made with additional drying time (approximately 24 h).

To prepare NO-releasing antimicrobial membranes, 2 wt % of chitosan was completely dispersed in 100 mL of 0.1N acetic acid. 2 wt % SNAP was dissolved in 80% ethanol and 3 ml of the resulting solution was added into the completely dispersed chitosan and the mixing process was continued to obtain complete encapsulation of SNAP. In another beaker 2 wt % of nanocellulose fibrils (CNF) was thoroughly dispersed in 100 mL of distilled (DI) water. Completely dispersed CNF and chitosan with SNAP were then homogeneously mixed together; while mixing them, 3 mL of 80% glycerol was added as a plasticizing agent. This mix was also degassed before casting the membrane. The 2-layer antimicrobial membranes were prepared by casting membrane without SNAP first and after 24 hours of drying, SNAP mixed chitosan and CNF homogeneous mix was poured on top of the partially dried membrane of without SNAP and air dried completely. For 3-layer membranes, the middle layer was made with SNAP and top and bottom were made without SNAP.

Physicochemical Characterizations

Water permeability: To determine water vapor permeability of the composite membranes the procedure followed by Jaya and Das[35] was used. Approximately 5 g of dehydrated silica gel was filled separately in 6 glass vials of uniform volume. The lid was replaced by one of the 6 membranes (2-layer with SNAP, 3-layer with SNAP, 2-layer control, 3-layer control, control chitosan and control CNF). All the vials were weighed and then placed in an environment maintained at 75% relative humidity (RH) and 22±2° C. established with saturated sodium chloride solution in a desiccator[36]. The weight of each vial containing the silica gel was recorded at 24 h intervals for 7 days, and the mean weight gained by the silica gel was calculated for each day. The water vapor permeability, K (kg·m/m²·day·Pa), of the composite membrane was calculated using the following equation.

$$K = \frac{dw/d\theta_P \times t}{A_P p^*}$$

where $dw/d\theta_p$ is the slope of curve plotted between the time $\theta_p$ (day) and cumulative moisture gain; w (kg) is the weight of the silica gel packed in the vials; t is the thickness of the film (m); $A_P$ (m²) is the surface area of the composite membranes; p* (Pa) is the saturation vapor pressure of water at 22° C.; the temperature of the environment chosen for the experiment and the relative humidity (75%).

Tensile strength: Mechanical attributes of the composite membranes were characterized in terms of tensile force using an Instron material testing machine (Instron model 5545, USA) with 1 kN load cell. Test specimens were cut according to the IPC-TM-650 standards with a 6:1 length to width ratio. Gauge length and thickness values were recorded individually for each sample, and carefully aligned to ensure minimal torsional forces were applied, and held by pneumatic jaws with 1"×1" against 1"×3" rubber faces. Specimens were tested at a constant extension rate of the cross head speed of 1 mm/s. The tests were done at 23±2° C. and 50±5% RH. Data points of force, distance and time were collected and analyzed for stress and strain relationships. Young's moduli of the composite membranes were derived from the stress and strain relationships. Tensile strength and Young's modulus were then calculated for each sample and averaged for each material. All materials were tested in triplicate.

Morphology Study Using Scanning Electron Microscopy

Film surface morphology and microstructure were examined using scanning electron microscopy (SEM) (FEI Inspect F FEG-SEM). Dried film samples were mounted on a metal stub with double-sided carbon tape and sputter coated with 10 nm gold-palladium using a Leica EM ACE200 sputter coater. Images were taken at accelerating voltage 20 kV and a magnification of 2000×.

NO Release Measurements

Nitric oxide release from the chitosan-nanocellulose composites were measured using a Sievers Chemiluminescence Nitric Oxide Analyzer (NOA) model 280i (Boulder, Colo.). The NOA has the ability to selectively measure NO through the reaction of NO with oxygen plasma, giving it the ability to reduce interference from molecules such as nitrates and nitrites[37]. The ability of NOA to selectively measure NO has made this technique a gold standard in the field of NO-releasing materials[38-40]. Films were punched to 5/16" diameter and threaded with silk surgical suture to be suspended in an amber NOA cell. The NOA cell with the membrane is lowered into a 37° C. water bath while the amber cell protects the sample from light. Deionized water (3 mL) was added to the NOA cell and allowed to heat to 37° C. Nitrogen was bubbled into the DI at 100 mL/min to provide a humid environment for the film. Both 2-layer and 3-layer membranes containing SNAP were tested for initial release, as well as after 24-hour storage in humid 37° C. conditions in water jacketed incubator (Thermo Fisher Scientific, Waltham, Mass. USA). A representation of the measurement cell is shown in FIG. 1.

Zone of inhibition (ZOI) studies: Antibacterial properties of SNAP incorporated chitosan-nanocellulose based packaging membranes were tested against three common bacterial strains using zone of inhibition (ZOI) assay. The bacteria used in the study were *Staphylococcus aureus* (*S. aureus*), *Listeria monocytogenes* (*L. monocytogenes*), and *Enterococcus faecalis* (*E. faecalis*). A modified version of agar diffusion standard protocol was followed to carry out this study aseptically[41,42]. A single isolated colony of each bacterium was suspended individually in Luria broth (LB) medium and allowed to grow at 37° C. for 14 hours at a rotating speed of 150 rpm using a shaker incubator. The optical density (OD) of the liquid suspension of each of the strains was measured by UV-Vis spectrophotometer (Genesis 10S-Thermo Scientific) at 600 nm ($OD_{600}$) using LB medium as blank and was adjusted to $1 \times 10^7$ colony forming units per ml (CFUs/ml) based on the calibration curve between CFUs and OD. A sterile swab was placed into the bacterial culture, gently pressed and rotated against the inside of the petridish (14 cm) to spread the bacteria uniformly and aseptically. The circular pieces (dia=14 mm) of packaging membranes (control and test) were placed over the bacterial culture and pressed gently. The resulting plates with bacterial strain and membranes were incubated overnight at 37° C. for 20 hours. The diameters of the ZOI of the membranes were compared with each other and among the bacteria strains to evaluate the antimicrobial effectiveness of the membranes.

Results and Discussion

Water vapor permeability characteristics analysis: Table 1 shows the water vapor permeability of the control and SNAP incorporated packaging membranes developed in this study. Control membranes prepared with a single material such as chitosan or CNF showed less water vapor permeability compared to the other membranes. Chitosan and CNF combined control membranes (2-layer and 3-layer) had slightly higher permeability than the membranes with single material even though their thickness is slightly higher than the single material control membranes. In ideal polymeric structures, gas and vapor permeability are independent of film thickness[43]. However, the result from chitosan and CNF membrane showed that it behaves like an ideal polymer. It is possible that during the permeability test, the side exposed to high relative humidity absorbed more water and developed desorption rate independent of the thickness-resistance for water vapor diffusion. As a result of this, the side exposed at low relative humidity became responsible for the vapor transfer. Under this condition, the diffusion flux could become independent of thickness and resulted in higher permeability than the single component control film[44]. SNAP incorporated membranes had higher water vapor permeability than the membranes prepared without SNAP. Even though the thickness of SNAP incorporated membranes with 2-layer and 3-layer were significantly higher than other control membranes, they demonstrated the highest permeability indicating that the membranes containing SNAP had a role in increasing the water vapor permeability. However, the water permeability values obtained in this study were lower than the methyl cellulose based biodegradable membranes developed by Turhan and Sahbaz[45] and other starch-based biodegradable films made by Para et al[46] and Bertizzi et al[44]. The addition of SNAP to the chitosan cellulose matrix likely decreases the attractive forces between the chain networks hence increasing the free volume and segmental motions, which could result in easy diffusion of water molecules and thereby increase the water vapor permeability.

Figure 2:
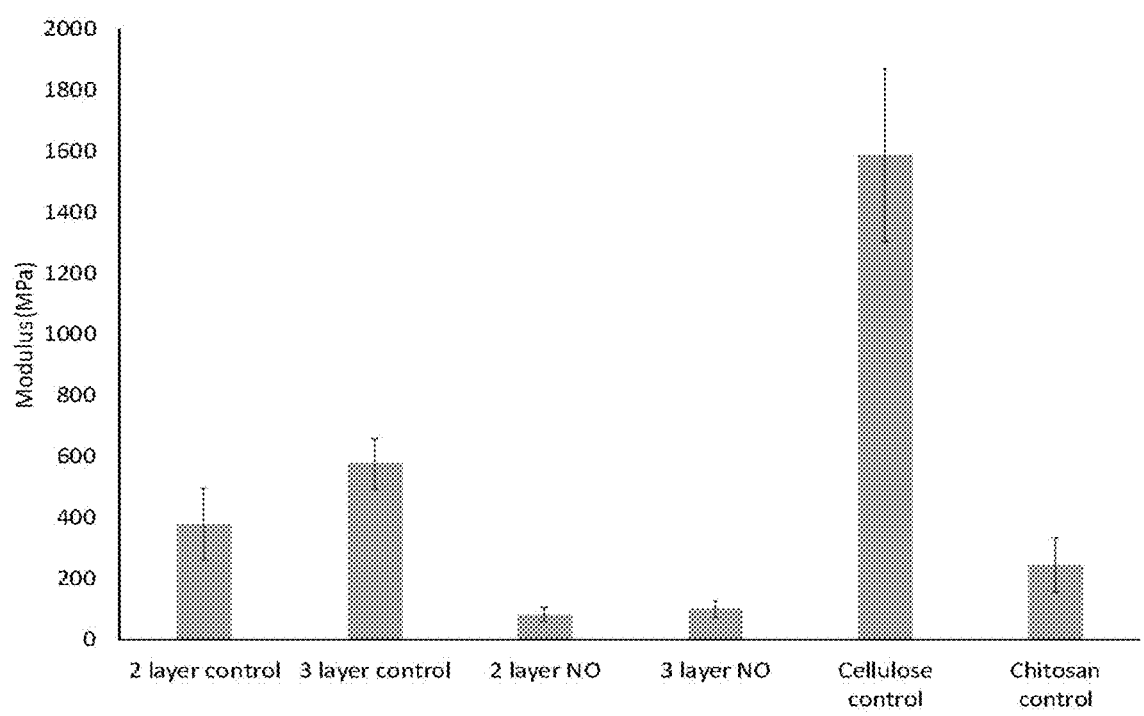
FIG. 2 is a graph of Young's Modulus of Nanocellulose-chitosan membranes.

Tensile strength analysis: FIG. 2 shows the Young's modulus measured for control and NO-releasing membranes. The mechanical strength of the membranes was studied by measuring their Young's modulus. Since nanocellulose possesses high mechanical strength, the membrane prepared with only nanocellulose showed highest Young's modulus (1587.6±282 MPa) as compared to the other membranes. Chitosan is structurally similar to cellulose except it contains an $NH_2$ group in the position of the $C_2$ hydroxyl group and mechanical properties of chitosan vary depending on the percentage of deacetylation[47]. Chitosan used in this study was 85% deacetylated and its Young's modulus was measured at 245.4±89 MPa. The 2-layer and 3-layer control films showed higher Young's modulus than control chitosan. As expected, chitosan and nanocellulose together increased the mechanical strength due to increased hydrogen bonding between the polymer chains of nanocellulose and chitosan[48]. However, incorporation of SNAP into the 2-layer and 3-layer membranes reduced the mechanical strength much lower than the control chitosan films. One of our previous studies showed similar reductions in strength upon incorporation of SNAP into medical grade polymers, which can arise due to the solubility of the SNAP molecule within the polymer matrix[49]. As the concentration of SNAP within the matrix surpasses the solubility limit, localized regions of SNAP crystallization occur[50]. The localized crystalline SNAP might create gaps between the nanocellulose network chains for its mobility and reduce inter-chain interactions leading to significant reduction in tensile strength of the membrane. Similar to the effect of SNAP on water vapor permeability, the addition of SNAP to the nanocellulose-chitosan matrix might decrease the attractive forces between the network chains and increase the free volume and segmental motions, which could cause a reduction in mechanical strength as well.

Figure 3:
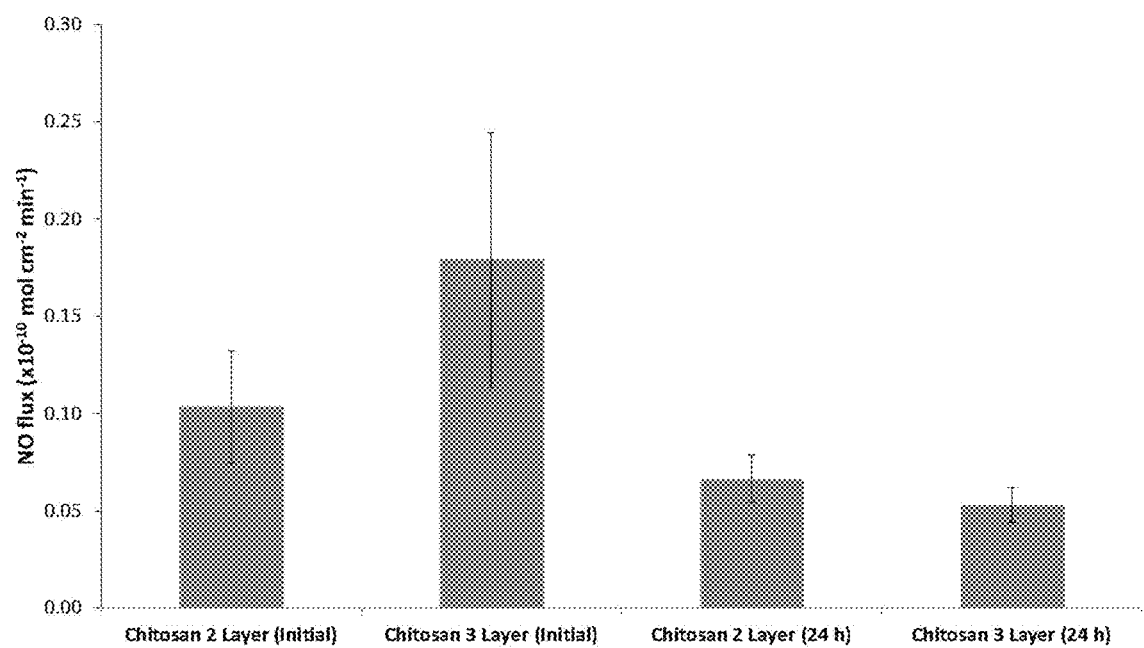
FIG. 3 is a graph of nitric oxide release rates of 2-layer and 3-layer chitosan-nanocellulose composites as measured by chemiluminescence.

NO release characteristics: Nitric oxide released from the 2-layer and 3-layer chitosan compositions were measured using the Sieves Chemiluminescence Nitric Oxide Analyzer (model 280i, Boulder, Colo.). The release of nitric oxide (NO) from SNAP is highly sensitive to heat, light (340 and 590 nm), and moisture, as these catalyze the spontaneous decomposition reaction[51, 52]. The 2-layer and 3-layer designs were implemented to see if the top layer of chitosan-nanocellulose would provide a barrier to help selectively deliver NO to one side of the film. This selective release of NO would be accomplished by limiting the exposure of the SNAP layer to both light and moisture. However, no significant difference was observed between the 2 and 3-layer configurations (p=0.36) as measured using a two-tailed Student's t-test. Release of NO from the chitosan-nanocellulose composites were measured for initial release, as well as a release after 24 hours to determine the level of NO that is being delivered during zone of inhibition studies (FIG. 3). All measurements were conducted at 37° C. and the samples were protected from light at all times.

Initial release of NO from the 2-layer and 3-layer composites were found to be $0.1 \pm 0.03 \times 10^{-10}$ mol $cm^{-2}$ $min^{-1}$ and $0.18 \pm 0.07 \times 10^{-10}$ mol $cm^{-2}$ $min^{-1}$ respectively. In both cases, release of NO decreased after 24 hours at 37° C. to $0.07 \pm 0.01 \times 10^{-10}$ mol $cm^{-2}$ $min^{-1}$ and $0.05 \pm 0.01 \times 10^{-10}$ mol $cm^{-2}$ $min^{-1}$. While the NO release appears to be higher for the 3-layer configuration, it is possible the NO release from the 2-layer configuration is asymmetric and is providing a larger flux of NO to the exposed SNAP layer than that of the chitosan-nanocellulose layer. This could result in an underestimation of the NO release.

Figure 4:
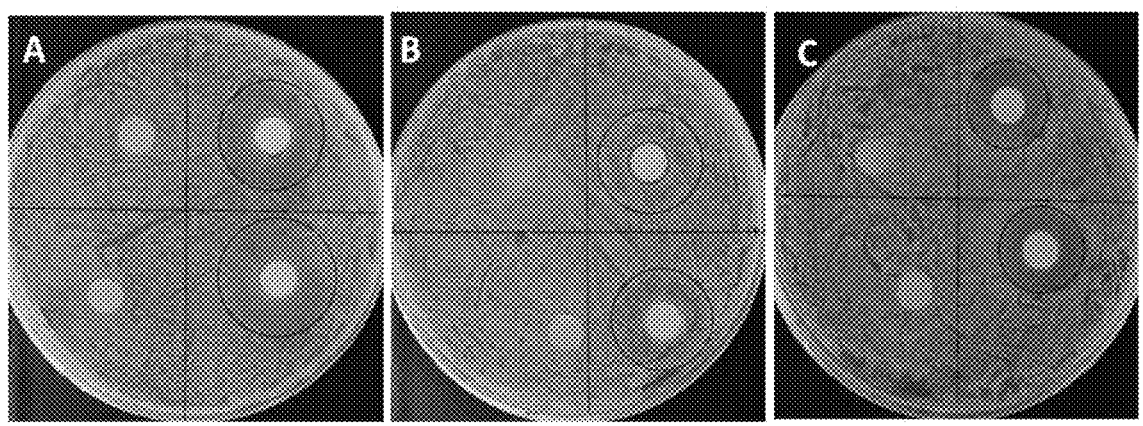
FIG. 4 is a set of images of the zone of inhibition comparison of 2-layer chitosan-CNF control, 2-layer SNAP incorporated chitosan-CNF film, 3-layer SNAP incorporated chitosan-CNF film and 3-layer control (clockwise from top left) for (A) *Listeria monocytogenes* (B) *Staphylococcus aureus* (C) *Enterococcus faecalis*.

Antibacterial characteristics evaluation: Table 2 shows the zone of inhibition (ZOI) of each selected bacterium strain for both 2 and 3 layer membranes with NO-releasing (SNAP) component as an antimicrobial agent. The chitosan-nanocellulose films with incorporated antimicrobial component resulted in the varying level of NO release, which resulted in ZOI (mm) with varied diameters (FIG. 4) depending on the level of NO release. As expected all bacterial strains (*S. aureus, L. monocytogenes*, and *E. faecalis*) were found susceptible to the packaging material owing to the bactericidal effect of NO. The antimicrobial activity of the membranes resulted in similar ZOI between 2-layer and 3-layer membranes against *E. faecalis*, and *S. aureus*. However, *L. monocytogenes* showed a significant difference in the ZOI between the 2-layer and 3-layer membranes. Among all the bacteria, *L. monocytogenes* was most susceptible to both the 3-layer and 2-layer membranes. Overall, *S. aureus* exhibited the smallest ZOI (as compared to *E. faecalis*, and *L. monocytogenes*). The higher antimicrobial activity of 3-layer membrane as compared to 2-layer membrane can directly be correlated to the NO flux exhibited by these films. As shown in FIG. 3, the 3-layer membranes have higher NO flux in the beginning which might have resulted in higher bacteria killing in the initial few hours. However, over an incubation period of 24 hours during ZOI testing, the NO flux reached almost the same value for both 2-layer and 3-layer membranes hence resulted in similar diameter of ZOI. The difference in the antimicrobial activity among the bacterial strains could be attributed to their cell membrane properties[53].

Figure 5:
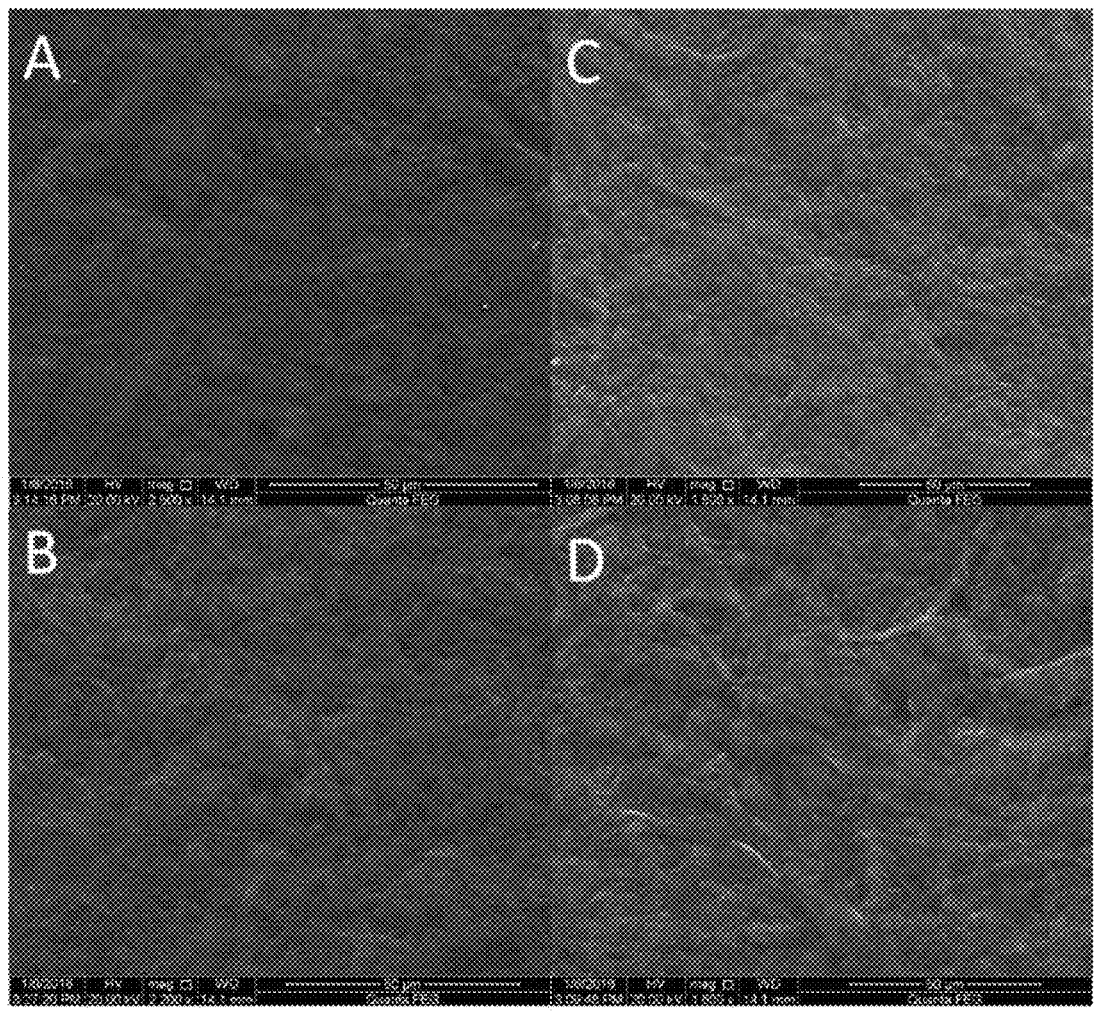
FIG. 5 is a set of scanning electron microscope images of the chitosan-nanocellulose film before and after addition of SNAP. A) 3-layer chitosan-nanocellulose, B) 2-layer chitosan-nanocellulose, C) 3-layer chitosan-nanocellulose with SNAP, and D) 2-layer chitosan-nanocellulose with SNAP.

Morphology of membranes: FIG. 5 shows the surface morphology of 2-layer and 3-layer control (A and B) membrane and the membrane with SNAP material (C and D). All of them show the nanocellulose fibrils network structure. It could be assumed that within the fibrils network chitosan was smoothly dispersed, because chitosan disperses within the nanocellulose matrix with relatively good interfacial adhesion between the two components[47] (Li et al., 2002). These results could be attributed to the strong interactions between nanocellulose fibrils and chitosan and SNAP, which are caused by the hydrogen bonding between the hydroxyl groups of nanocellulose and carbonyl group in the chitosan.

S-nitroso-N-acetylpenicillamine incorporated antimicrobial membranes mixed with nanocellulose fibrils and chitosan were successfully fabricated. Developed membranes exhibited good film forming properties due to the presence of high density of amino groups and hydroxyl groups and inter and intramolecular hydrogen bonding. The chitosan-CNF—NO-releasing composites showed antimicrobial characteristics in the packaging membranes. The addition of chitosan and SNAP into nanocellulose to develop composite biodegradable membrane with antimicrobial activity showed clear effects towards inhibition of *E. faecalis, S. aureus*, and *L. monocytogenes* as shown using ZOI. The membranes developed in this study showed excellent water barrier property with a low value of water vapor permeability. Surface morphology showed the strong interactions between nanocellulose fibrils, chitosan, and SNAP materials. Tensile strength measurements showed decreased Young's modulus for SNAP incorporated membranes, which would be further studied to improve its mechanical properties.

REFERENCES

U.S. Department of Health and Human Services and U.S. Department of Agriculture, *Dietary Guidelines for Americans*, January 2005.

U.S. Department of Agriculture and Centers for Disease Control and Prevention, "MyPyramid, April 2005.

U.S. Department of Agriculture, Economic Research Service, U.S. per Capita Food Consumption of Fruits and Vegetables, 2005.

Produce Marketing Association, "Fresh-cut Produce Industry" fact sheet, 2006. See web site at http://www.pma.com/.

Mead, P. S.; Slutsker, L.; Dietz, C. 2000. Food-Related Illness and Death in the United States. *Journal of Environmental Health*. 2000, 62, 9-18.

Allos, B. M.; Moore, M. R.; Griffin, P. M.; Tauxe, R. V. Surveillance for Sporadic Foodborne Disease in the 21st Century: The FoodNet Perspective. *Clinical Infectious Disease*. 2004, 38(3), 5115-120.

Lampel, K. A.; Orlandi, P. A.; Kornegay, L. Improved Template Preparations for PCR-Based Assays for Detection of Food-Borne Bacterial Pathogens. *Applied and Environmental Microbiology*. 2000, 66(10), 4539-4542.

Sivapalasingam, S.; Friedman, C. R.; Cohen, L.; Tauxe, R. V. Fresh Produce: A Growing Cause of Outbreaks of Foodborne Illness in the United States, 1973 through 1997. *Journal of Food Protection*. 2004, 67(10), 2342-2353.

Tauxe, R. V. Emerging Foodborne Pathogens. *International Journal of Food Microbiology*. 2002, 78, 31-41.

Trevejo, R. T; Courtney, J. G.; Starr, M.; Vugia, D. J. Epidemiology of Salmonellosis in California, 1990-1999: Morbidity, Mortality, and Hospitalization Costs. *American Journal of Epidemiology*. 2003, 157:48-57.

Leceta, I.; Gurrero, P.; Ibarburu, I.; Dueñas, M. T.; Caba, K. Characterization and antimicrobial analysis of chitosan-based films. *J. Food Eng*. 2013, 116, 889-899.

Sung, S. Y.; Sin, L. T.; Tee, T. T.; Bee, S. T.; Rahmat, A. R.; Vikhraman, M. Antimicrobial agents for food packaging applications. *Trends. FoodSci. Technol*. 2013, 33, 110-123.doi:10.1016/j.tifs.2013. 08.001

Türe, H.; Gallstedt, M.; Hedenqvist, M. K. Antimicrobial compression-molded wheat gluten films containing potassium sorbate. *Food Res. Int*. 2012, 45, 109-115.

Zhong, Y.; Song, X.; Li, Y. Antimicrobial, physical and mechanical properties of kudzu starch-chitosan composite films as a function of acid solvent types. *Carbohydr. Polym*. 2011, 84, 335-342.

Suppakul, P.; Miltz, J.; Sonneveld, K.; Bigger, S. W. Active packaging technologies with an emphasis on antimicrobial packaging and its applications. *J. Food. Sci*. 2003, 68, 408-420.

Iwamoto, S., Abe, K.; Yano, H. The effect of hemicellulose on wood pulp nanofibrillation and nanofiber network characteristics. *Biomacromolecules*. 2008, 9:1022-1026.

Suryanegara, L.; Nakagaito, A. N.; Yano, H. The effect of crystallization of PLA on the thermal and mechanical properties of microfibrillated cellulose-reinforced PLA composites. *Compos Sci Technol*. 2009, 69:1187-1192.

Nakagaito, A. N.; Fujimura, A.; Sakai, T.; Hama, Y.; Yano, H. Production of microfibrillated cellulose (MFC)-reinforced polylactic acid (PLA) nanocomposites from stets obtained by a papermaking-like process. *Comp Sci Techn*. 2009, 69:1293-1297.

Jonoobi, M.; Harun, J.; Mathew, A. P.; Oksman, K. Mechanical properties of cellulose nanofiber (CNF) reinforced polylactic acid (PLA) prepared by twin screw extrusion. *Composites Science and Technology*. 2010, 70(12), 1742-1747.

George, j.; Ramana, K. V.; Sabapathy, S. N.; Bawa, A. S. Physicomechanical properties of chemically treated bacterial (*Acetobacter xylinum*) cellulose membrane. *World J. Alicrob. Biot*. 2005, 21, 1323-1327.

Avik Khan.;, Tanzina Huq.; Ruhul A. Khan.; Bernard Riedl.; Monique Lacroix. Nanocellulose-Based Composites and Bioactive Agents for Food Packaging. *Critical Reviews in Food Science and Nutrition.* 2014, 54:163-174.

Debeaufort, F.; Voilley, A. Lipid based edible films and coatings," in Edible Films and Coatings for Food Applications, M. E. Embuscado and K. C. Huber, Eds., 2009, pp. 135-168, Springer, New York, N.Y., USA.

McHugh, T. H.; Avena-Bustillos, R. J. Applications of edible films and coatings to processed foods," in Edible Coatings and Films to Improve Food Quality, E. A. Baldwin, R. Hagenmaier, and J. Bai, Eds., 2012, pp. 291-318, CRC Press, Boca Raton, Fla., USA.

Soliva-Fortuny, R.; Rojas-Graii, M. A.; Martin-Belloso, O. Polysaccharide coatings," in Edible Coatings and Films To Improve Food Quality, E. Baldwin, R. Hagenmaier, and J. Bai, Eds., 2012, pp. 103-136, CRC Press, Boca Raton, Fla., USA.

Appendini, P.; Hotchkiss, J. H. Review of antimicrobial food packaging. *Innovative Food Sci. Emerging. Technol.* 2002, 3, 113-126.

Miranda, K. M.; Espey, M. G.; Jourd'heuil, D.; Grisham, M. B.; Fukuto, J. M.; Feelisch, M.; Wink, D. A. The chemical biology of nitric oxide. In Ignarro, L. J. (ed.), Nitric Oxide: Biology and Pathobiology, Academic Press, San Diego, Calif., 2000, pp. 41-55.

Cammack, R.; Joannou, C. L.; Cui, X. Y.; Martinez, C. T.; Maraj, S. R.; Hughes, M. N. Nitrite and nitrosyl compounds in food preservation. *Biochimica and Biophysica Acta-Bioenergetics.* 1999, 1411, 475-488.

Kanner, J.; Juven, B. J. S-nitrosocysteine as an antioxidant, color-developing, andanticlostridial agent in comminuted turkey meat. *Journal of Food Science.* 1980, 45, 1105-1108, 1112.

De Groote, M. A.; Fang, F.C. NO inhibitions: antimicrobial properties of nitric oxide. *Clin Infect Dis.* 1995, 21 (2), S162-5.

Jones, M. L.; Ganopolsky, J. G.; Labbé, A.; Wahl, C.; Prakash, S. Antimicrobial properties of nitric oxide and its application in antimicrobial formulations and medical devices. *Appl. Microbiol. Biotechnol.* 2010, 88, 401-407.

Schairer, D.; Martinez, L. R.; Blecher, K.; Chouake, J.; Nacharaju, P.; Gialanella, P.; Friedman, J. M.; Nosanchuk, J. D.; Friedman, A. J. Nitricoxidenanoparticles: preclinical utility as a therapeutic for intramuscular abscesses. *Virulence* 2012, 3, 62-67.

Nathan, C. Reactive oxygen and nitrogen intermediates in the relationship between mammalian hosts and microbial pathogens. *Proc Natl Acad Sci USA.* 2000. 97, 8841-8.

Privett, B. Examination of bacterial resistance to exogenous nitric oxide. *Nitric Oxide.* 2012. 26, 169-173.

Friedman, A. Susceptibility of gram-positive and -negative bacteria to novel nitric oxide-releasing nanoparticles. *Virulence.* 2011. 3(6), 45-50.

Jaya, S.; Das, H. Accelerated storage, shelf life and color of mango powder. *Journal of Food Processing and Preservation.* 2005, 29, 45-62.

Labuza, T. P. *Moisture Sorption: Practical Aspects of Isotherm Measurement and Use.* American Association of Cereal Chemists, 1984, Minnesota.

Coneski, P. N; Schoenfisch, M. H. Nitric oxide release: part III. Measurement and reporting. *Chemical Society Reviews.* 2012, 41, 3753-8.

Brisbois, E. J.; Handa, H.; Major, T. C.; Bartlett, R. H.; Meyerhoff, M. E. Long-term nitric oxide release and elevated temperature stability with S-nitroso-N-acetylpenicillamine (SNAP)-doped Elast-eon E2As polymer. *Biomaterials.* 2013, 34, 6957-66.

Handa, H.; Brisbois, E. J.; Major, T. C.; Refahiyat, L.; Amoako, K. A.; Annich, G. M. In vitro and in vivo study of sustained nitric oxide release coating using a diazeniumdiolate-doped poly (vinyl chloride) matrix with the poly (lactide-co-glycolide) additive. *Journal of Materials Chemistry B.* 2013, 1, 3578-87.

Handa, H.; Major, T. C.; Brisbois, E. J.; Amoako, K. A.; Meyerhoff, M. E.; Bartlett, R. H. Hemocompatibility comparison of biomedical grade polymers using rabbit thrombogenicity model for preparing nonthrombogenic nitric oxide releasing surfaces. *Journal of Materials Chemistry B.* 2014, 2, 1059-67.

Ericsson, H.; Tunevall, G.; Wickman, W. The Paper Disc Method for Determination of Bacterial Sensitivity to Antibiotics: Relationship between the diameter of the zone of inhibition and the minimum inhibitory concentration. *Scandinavian Journal of Clinical and Laboratory Investigation.* 1960, 12(4), 414-422.

Rajni Singh; Astha Jain; Shikha Panwar; Deepti Gupta; Khare, S. K. Antimicrobial activity of some natural dyes. *Dyes and Pigments.* 2005, 66 (2), 99-102.

Schwartzberg, H. G. Modeling of gas and vapor transport through hydrophilic films. In M. Mathlouthi (Ed.), Food packaging and preservation. Theory and practice, 1986, pp. 115-136. London: Elsevier Applied Science Pub.

Bertuzzi, M. A.; Castro Vidaurre, E. F.; Armada, M.; Gottifredi, J. C. Water vapor permeability of edible starch based films. *Journal of Food Engineering.* 2007, 80, 972-978

Nazan Turhan, K.; Ferhunde Sahbaz. Water vapor permeability, tensile properties and solubility of methylcellulose-based edible films. *Journal of Food Engineering.* 2004, 61, 459-466

Parraa, D. F.; Tadinib, C. C.; Poncea, P.; Lugãno. A. B. Mechanical properties and water vapor transmission in some blends of cassava starch edible films. *Carbohydrate Polymers.* 2004, 58, 475-481

Wenling, C.; Duohui, J.; Jiamou, L.; Yandao, G.; Nanming, Z.; Xiufang, Z. Effects of the degree of deacetylation on the physicochemical properties and Schwann cell affinity of chitosan films. *J Biomater Appl.* 2005, 20(2), 157-77.

Li, Z.; Zhuang, X. P.; Liu, X. F.; Guan, Y. L.; Yao, K. D. Study on antibacterial O-carboxymethylated chitosan/cellulose blend film from LiCl/N, N-dimethylacetamide solution. *Polymer.* 2002, 43, 1541-1547.

Goudie, M. J.; Brisbois, E. J.; Pant, J.; Thompson, A.; Potkay, J. A.; Handa, H. Characterization of an S-nitroso-N-acetylpenicillamine-based nitric oxide releasing polymer from a translational perspective. *International Journal of Polymeric Materials and Polymeric Biomaterials.* 2016, Article in press.

Wo, Yaqi. Origin of Long-Term Storage Stability and Nitric Oxide Release Behavior of CarboSil Polymer Doped with S-Nitroso-N-acetyl-D-penicillamine. *ACS applied materials & interfaces.* 2015, 40(7), 22218-22227.

Lyn H áWilliams, D. Identification of Cu+ as the effective reagent in nitric oxide formation from S-nitrosothiols (RSNO). *Journal of the Chemical Society, Perkin Transactions.* 1996, 2 (4), 481-487.

Frost, Megan C.; Mark E. Meyerhoff. Controlled photoinitiated release of nitric oxide from polymer films containing S-nitroso-N-acetyl-DL-penicillamine derivatized fumed silica filler. *Journal of the American Chemical Society.* 2004, 126(5), 1348-1349.

Hervé Roy. Tuning the properties of the bacterial membrane with aminoacylated phosphatidyl glycerol. *IUBMB Life.* 2009, 61(10), 940-953.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A multilayer packaging film comprising
at least one layer comprising:
   an antibacterially effective amount of a monomer or polymer comprising an S-nitrosothiol group, wherein the weight percent of the monomer or polymer is from about 0.1% to about 10%; and
   about 90-99.9 weight percent of a biodegradable polymer comprising a nanocelluslose and a chitosan, wherein the weight ratio of chitosan to nanocellulose is from 10:1 to 1:10.

2. The packaging film of claim 1 wherein the monomer or polymer is a monomer.

3. The packaging film of claim 2 wherein the monomer comprises an amino acid moiety.

4. The packaging film of claim 3 wherein the monomer is S-Nitrosoglutathione or S-Nitroso-N-acetylpenicillamine; or a salt, or derivative thereof.

5. The packaging film of claim 4 wherein the monomer is S-Nitroso-N-acetylpenicillamine.

6. The packaging film of claim 1 further comprising at least one layer substantially free of polymer or monomer comprising an S-nitrosothiol group.

7. A method of preparing a packaging film comprising combining a packaging film of claim 1 and at least one other packaging film layer.

8. A method for preserving a foodstuff comprising enclosing the foodstuff in the packaging film of claim 1.

9. The packaging film of claim 1, wherein the weight ratio of chitosan to nanocellulose is about 1:1.

10. The packaging film of claim 1, wherein the at least one layer consists of:
    about 0.1% to about 10% of a monomer or polymer comprising an S-nitrosothiol group; and
    about 90-99.9 weight percent of a biodegradable polymer consisting of a nanocelluslose, a chitosan and a plasticizer, wherein the weight ratio of chitosan to nanocellulose is about 1:1.

11. The packaging film of claim 1, wherein the at least one layer comprising a monomer or polymer comprising an S-nitrosothiol group is a first layer and wherein the packaging film further comprises a second layer comprising the biodegradable polymer comprising a nanocelluslose and a chitosan, wherein the second layer is substantially free of polymer or monomer comprising an S-nitrosothiol group.

12. The packaging film of claim 11, further comprising a third layer comprising the biodegradable polymer comprising a nanocelluslose and a chitosan wherein the third layer is substantially free of polymer or monomer comprising an S-nitrosothiol group, wherein the first layer is sandwiched between the second and third layers.

13. The packaging film of claim 1, wherein the packaging film has a tensile strength from 0.1 to 4.0 GPa at 23° C. and 50% relative humidity.

14. The packaging film of claim 1, wherein the packaging film has a water transport through the film of about 1 $g/m^2 \cdot day$ to about 50 $g/m^2 \cdot day$ as measured under an accelerated condition of 40° C. and 90% relative humidity.

15. The packaging film of claim 1, wherein the packaging film has an oxygen transport through the film of about 2700 to 0.3 $cm^3/m^2 \cdot day \cdot atm$ at 20° C. temperature and 65% relative humidity.

16. The packaging film of claim 1, wherein the packaging film has an NO release rate from about $10^{-11}$ to $10^{-9}$ $mol/cm^2$-min.

* * * * *